United States Patent
Franke et al.

(10) Patent No.: US 10,796,465 B2
(45) Date of Patent: Oct. 6, 2020

(54) METHOD FOR ESTABLISHING AND/OR REDUCING ARTIFACTS, METHOD FOR ESTABLISHING A LOCAL CONCENTRATION DISTRIBUTION AND SYSTEM FOR VISUALLY REPRESENTING A CORRECTED OVERALL IMAGE DATA RECORD

(71) Applicant: Bruker BioSpin MRI GmbH, Ettlingen (DE)

(72) Inventors: Jochen Franke, Karlsruhe (DE); Michael Herbst, Freiburg (DE)

(73) Assignee: BRUKER BIOSPIN MRI GMBH, Ettlingen (DE)

( * ) Notice: Subject to any disclaimer, the term of this patent is extended or adjusted under 35 U.S.C. 154(b) by 84 days.

(21) Appl. No.: 16/351,708

(22) Filed: Mar. 13, 2019

(65) Prior Publication Data
US 2019/0287277 A1 Sep. 19, 2019

(30) Foreign Application Priority Data
Mar. 13, 2018 (DE) .................... 10 2018 203 786

(51) Int. Cl.
G06K 9/00 (2006.01)
G06T 11/00 (2006.01)

(52) U.S. Cl.
CPC .......... G06T 11/008 (2013.01); G06T 11/006 (2013.01); *G06T 2211/424* (2013.01)

(58) Field of Classification Search
None
See application file for complete search history.

(56) References Cited

U.S. PATENT DOCUMENTS 8,423,125 B2 * 4/2013 Rousso ................ A61B 6/583
600/436
9,364,165 B2 6/2016 Gleich
(Continued)

FOREIGN PATENT DOCUMENTS

| DE | 102015214071 B3 | 7/2015 |
|---|---|---|
| EP | 2906118 B1 | 4/2014 |
| WO | 2013088413 A1 | 6/2013 |

OTHER PUBLICATIONS

Rahmer et al., "First experimental evidence of the feasibility of multi-color magnetic particle imaging"; Phys.Med.Biol. 60 (2015) 1775-1791.
(Continued)

*Primary Examiner* — Hadi Akhavannik
(74) *Attorney, Agent, or Firm* — Edell, Shapiro & Finnan, LLC

(57) ABSTRACT

A method for establishing and/or reducing artifacts that arise when reconstructing (R) an MPI overall image data record from MPI signal data and an appended system matrix (SMapp(r,f)), wherein the appended system matrix (SMapp(r,f)) includes system matrices of different particle classes (P1, P2). The method includes setting a selection region ($c_{vn}(r)$) of a reconstructed MPI overall image data record ($c_n(r)$), producing virtual signal data ($s_n(f)$) by inverse transformation of the selection region, reconstructing a virtual overall image data record ($c'_{vn}(r)$) from the virtual signal data and the appended system matrix, setting an artifact region ($c_{artifact\_n}(r)$) within the reconstructed virtual overall image data record so that the artifact region has only voxels lying outside of the selection region, and assigning the image data present in the artifact region as artifact image data ($c_{artifact\_n}(r)$). This permits ghost artifacts to be corrected.

17 Claims, 13 Drawing Sheets

(56) References Cited

U.S. PATENT DOCUMENTS

| | | | |
|---|---|---|---|
| 10,016,146 B2* | 7/2018 | Weber | A61B 5/0515 |
| 2011/0246103 A1* | 10/2011 | Rahmer | A61B 5/05 |
| | | | 702/57 |
| 2012/0153948 A1* | 6/2012 | Rahmer | A61B 5/0515 |
| | | | 324/301 |
| 2012/0197115 A1 | 8/2012 | Pasmans et al. | |
| 2017/0020407 A1 | 1/2017 | Weber | |
| 2017/0108560 A1* | 4/2017 | Weber | A61B 5/0515 |
| 2019/0285710 A1* | 9/2019 | Franke | A61B 5/0515 |
| 2019/0287277 A1* | 9/2019 | Franke | G06T 11/006 |

OTHER PUBLICATIONS

Stehnig et al., "Simultaneous Magnetic Particle Imaging (MPI) and Temperature Mapping using Multi-Color MPI"; International Journal of Magnetic Particle Imaging 2, No. 2 (2016).

Grüttner et al., "On the formulation of the image reconstruction problem in magnetic particle imaging"; Biomedical Engineering/Biomedizinische Technik; vol. 58, Issue 6 (Dec. 2013).

Knopp et al., "Sparse reconstruction of the Magnetic Particle Imaging System Matrix"; EEE Transactions on MEdical Imaging; vol. 32 Issue: 8.

* cited by examiner

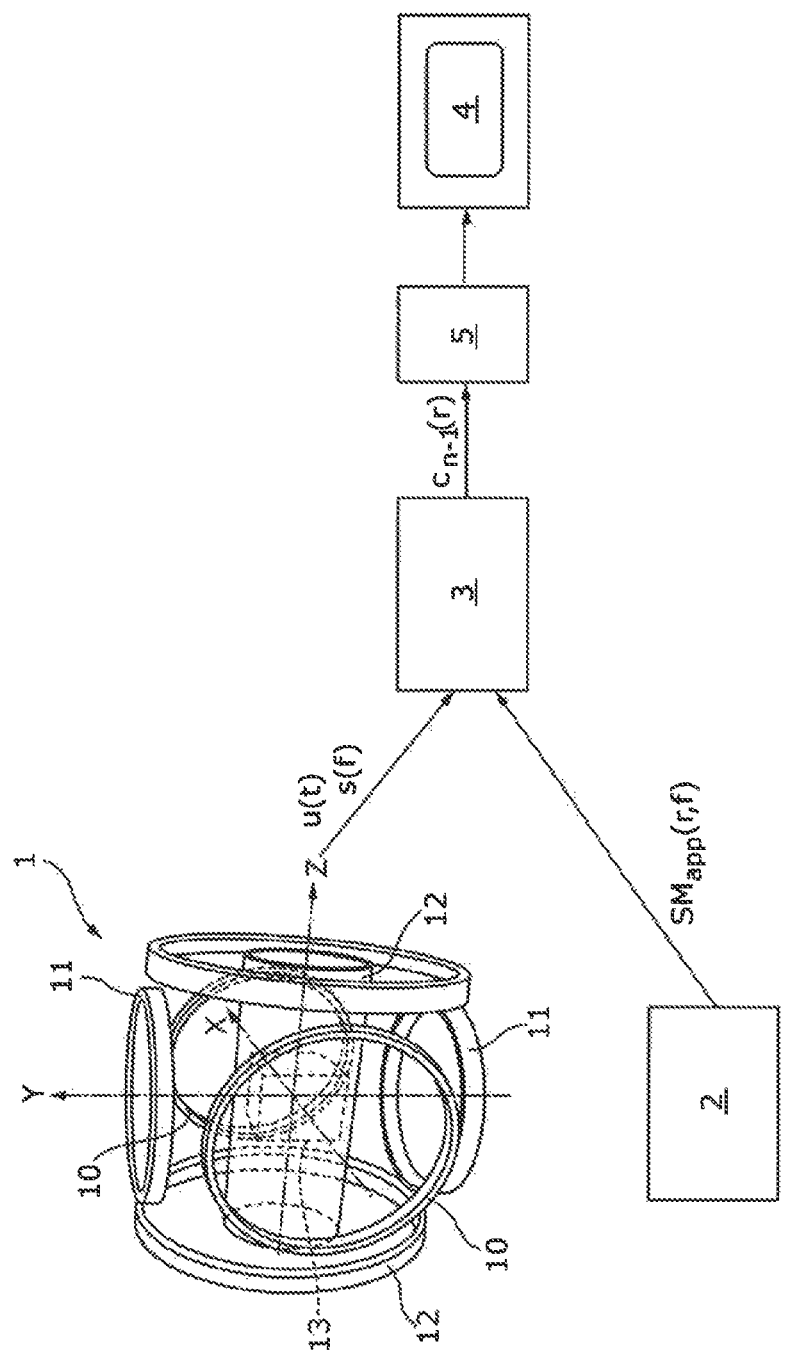

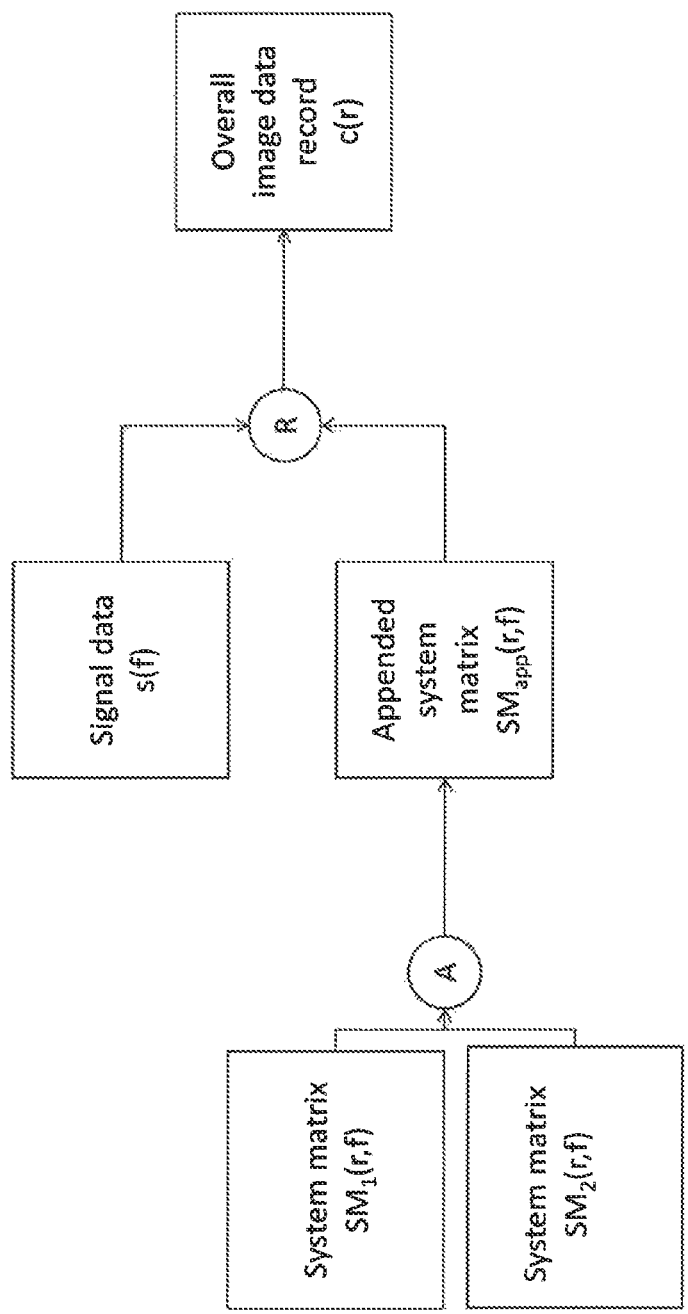

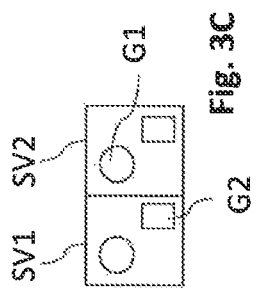
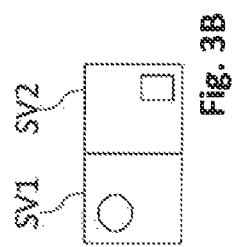
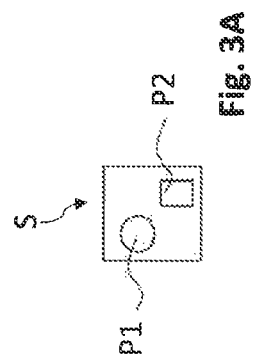

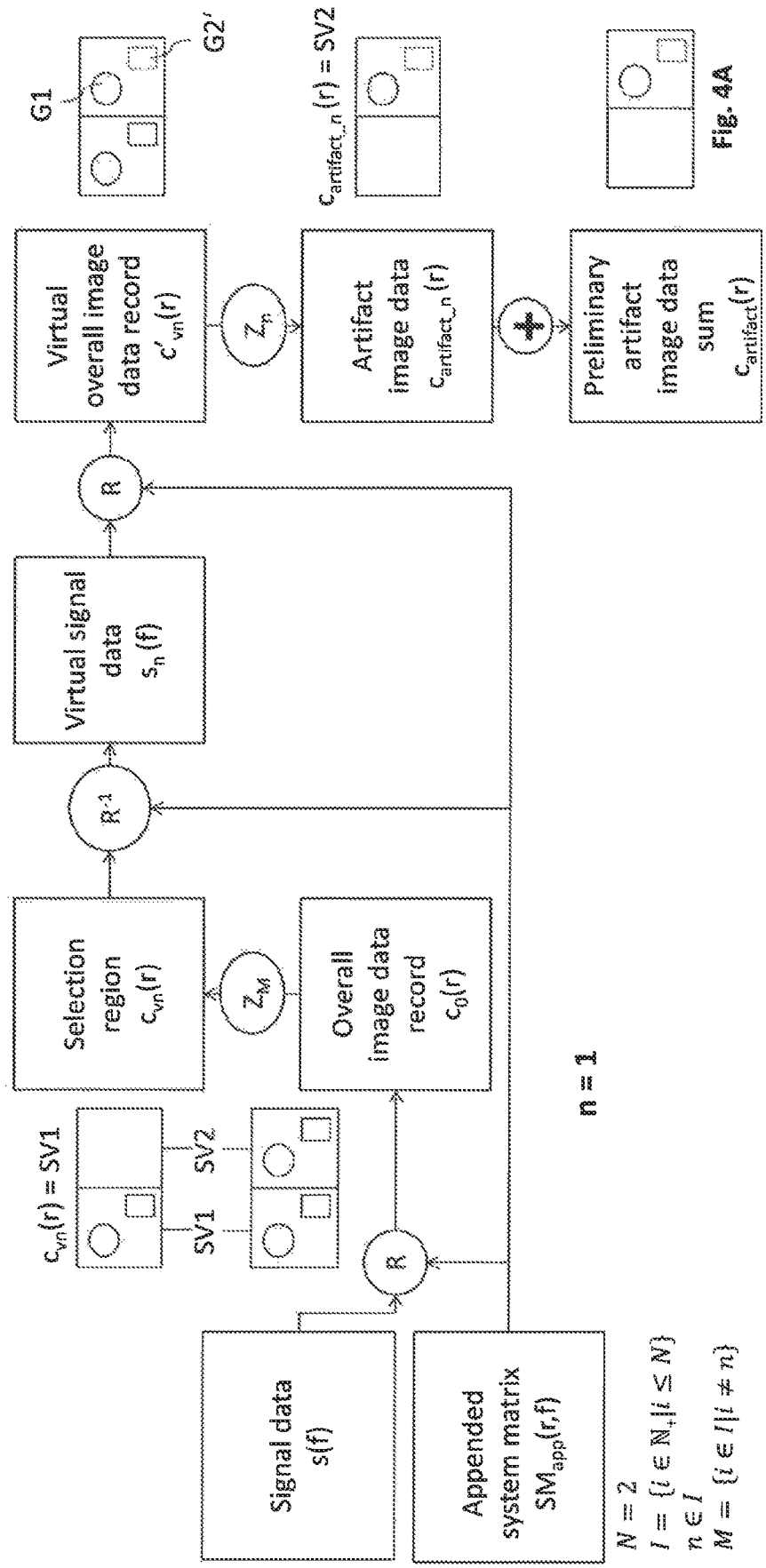

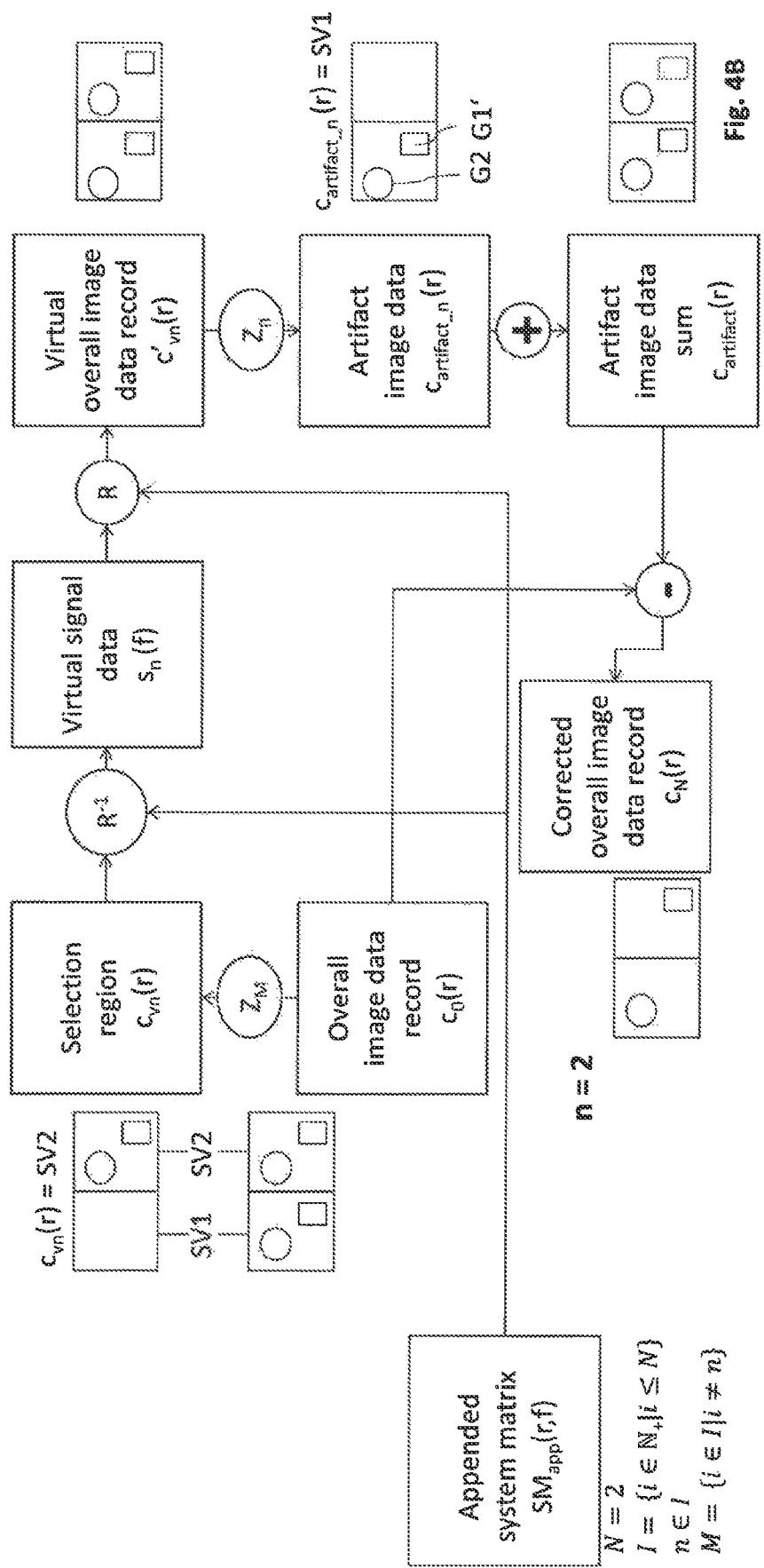

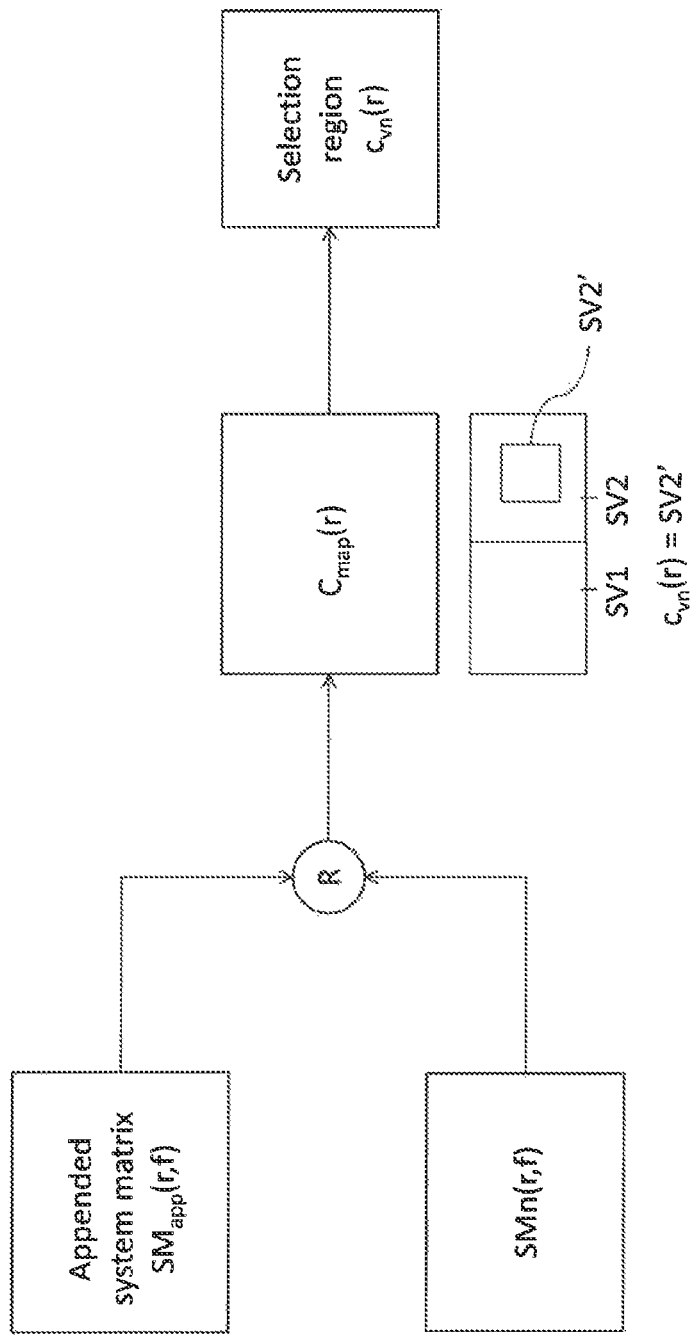

METHOD FOR ESTABLISHING AND/OR REDUCING ARTIFACTS, METHOD FOR ESTABLISHING A LOCAL CONCENTRATION DISTRIBUTION AND SYSTEM FOR VISUALLY REPRESENTING A CORRECTED OVERALL IMAGE DATA RECORD

CROSS REFERENCE TO RELATED APPLICATIONS

This application claims foreign priority under 35 U.S.C. § 119(a)-(d) to German Application No. 10 2018 203 786.8 filed on Mar. 13, 2018, the entire contents of which are hereby incorporated into the present application by reference.

FIELD OF THE INVENTION

The invention relates to a method for establishing and/or reducing artifacts that arise when reconstructing an MPI overall image data record from MPI signal data and an appended system matrix, wherein the appended system matrix comprises system matrices of different particle classes. The invention also relates to a method for establishing a local concentration distribution and a system for visually representing a corrected overall image data record.

BACKGROUND

A spatially dependent magnetic field with a field-free region is applied in the case of magnetic particle imaging (MPI) measurements. By applying a magnetic drive field, the field-free region is moved through an examination volume along a trajectory with the aid of a measurement sequence in a drive-field region. The drive-field region is defined by the trajectory and part of the examination volume, with the examination volume (FOV) being defined by a reconstruction region, i.e., the region in which image data are intended to be reconstructed, optionally (e.g., within the scope of an overscan) without selected regions. The signal responses of magnetic particles, preferably superparamagnetic iron oxide particles (SPION) are measured as MPI signal data. The measured signal data should be viewed as a summed signal of all excited particles. These are measured in the time domain and transformed into the frequency domain by a Fourier transform. A reconstruction is carried out to produce the MPI overall image data record.

The MPI overall image data record comprises image data of particles of different particle classes within the examination volume. In the case of a system-function-based MPI image reconstruction, knowledge of a spatially encoded system response (frequency response), a so-called system function, is necessary, the latter describing the relationship between the measurement signal (MPI signal data) and, for example, the particle distribution of a certain particle class (mapping the particle concentration on a measured frequency response). As a rule, the system function is available as a system matrix. The system matrix is provided for a system matrix region that comprises the part of the image space within which MPI image data should be reconstructed. The system matrix (SM(r,f)) provides the basis functions which describe the spatially dependent particle signal response (F(u(t)) or s(f)) of the particle concentration distribution (c(r)). The system matrix is determined independently of the actual object measurement (e.g., by calibration measurement, by simulation, by hybrid approaches). If the system matrix is determined experimentally (e.g., with a calibration measurement), the particle signal response of an (ideally punctiform) calibration sample is measured at a large number of spatial positions within a system matrix region. This calibration process requires long recording times. On account of the size of the obtained system matrix (SM(r,f)), the solution to the reconstruction problem is computationally expensive and time-consuming. For the purposes of calculating the concentration distribution (c(r)) of the magnetic particles in the reconstruction region, a system of equations F (u(t))=SM(r,f)·c(r) must be solved. The concentration distribution c(r) of the employed magnetic particles within the examination volume can be calculated by suitable reconstruction methods (e.g. [Grüttner]). This step is preferably carried out using a so-called "linear solver" (e.g., Kaczmarz algorithm). Consequently, a particle concentration (c(r)) can be determined, for example quantitatively, for each voxel within the drive-field region.

Below, a particle class should be understood to mean magnetic particles that have a certain signal behavior during an MPI measurement, i.e., have a similar signal response behavior. If a particle system differs in at least one parameter that influences the particle signal response, it thus forms different particle classes. In order to be able to distinguish between different particle classes, a plurality of system matrices are acquired, wherein the employed punctiform probe differs in at least one of the aforementioned parameters per system matrix. That is to say, it is necessary to establish a plurality of system matrices (at least two system matrices) to determine different parameters through MPI.

[Rahmer] and US 2012/0197115 A1 describe a method with which signals from different particle types or particles can be separated in different surroundings. According to [Rahmer], different system matrices are juxtaposed and form an appended system matrix.

$$\hat{C} = [\hat{C}_A \hat{C}_B \ldots ] = \hat{S}[\hat{G}_A \hat{G}_B \ldots ]^{-1}$$

A multi-parameter space can be produced by appending a plurality of system matrices of different particle classes to form an appended matrix. That is to say, image data of particles of different particle classes can be presented in different partial volumes. Each partial volume comprises image data of a particle class for the same predetermined examination volume in real space. Preferably, the system matrices are established for the same examination volume (FOV) and with the same resolution, i.e., the same space discretization (voxel size) and the same frequency discretization ((geometric) size of the system matrix divided by the number of voxels in the respective dimension). If the system matrices to be linked have different resolutions and/or were established for different examination volumes, an interpolation and/or FOV adaptations (cutting, zero padding, . . . ) is carried out to match the resolutions of the system matrices to one another.

The sum of the partial volumes yields the sum of the concentration distribution, i.e., the overall concentration distribution without distinguishability of the particle classes. Thus, for example, the concentration of particles of a certain particle class within the examination volume can be represented in a partial volume. Then, the sum of these partial volumes would yield an image data record that reproduces the overall concentration of the magnetic particles.

Consequently, the signal equation is:

$$F(u(t)) = [SM_1 \ldots SM_n] \begin{bmatrix} C_{P1} \\ \ldots \\ C_{Pn} \end{bmatrix} = SM_{appended} C_{appended}$$

The concentration distribution $c_{appended}(x)$ of the magnetic particles in the image space is obtained after solving the overall system of equations: $F(u(t))=SM_{appended}\cdot c_{appended}(x)$, where $F(u(t))$ is the Fourier transform of the measured signal.

Consequently, a particle concentration is determined quantitatively for each voxel within the examination volume, with the linear solver seeking out the optimal solution in which the particle signals of different particle classes are reconstructed in the best-possible fitting partial volume, i.e., generate the smallest error term. If the system matrices are similar in their totality or in individual frequency components, this leads to a reconstruction of concentration components in all corresponding partial volumes. In the case of particle classes which fit to both the one system matrix and the other system matrix, concentrations are therefore reconstructed in both partial volumes. As a consequence thereof, the signal of one particle class is reconstructed as a "ghost artifact" in the partial volumes of other particles, as can be identified in [Rahmer]. Thus, "ghost artifacts" denote concentrations represented in one partial volume that should in fact be represented in another partial volume.

These ghost artifacts represent a problem in respect of the quantification of the individual particle classes. Moreover, such ghost artifacts may make object determination, for example within the scope of catheter tracking, more difficult.

SUMMARY

An object of the invention is to propose a method that can be used to establish and/or reduce or correct ghost artifacts.

According to the invention, this object is achieved by a method comprising the following method steps:
a) setting a selection region of a reconstructed MPI overall image data record;
b) producing virtual signal data by an inverse transformation of the selection region;
c) reconstructing a virtual overall image data record from the virtual signal data and the appended system matrix;
d) setting an artifact region within the reconstructed virtual overall image data record in such a way that the artifact region only comprises voxels lying outside of the selection region;
e) assigning the image data present in the artifact region as artifact image data.

An MPI overall image data record should be understood to mean a data record which contains image data for all partial volumes corresponding to the system matrices employed for the reconstruction. In contrast thereto, the selection region comprises fewer image data, for example image data for fewer partial volumes. Establishing an MPI overall image data record comprises the following method steps:
providing signal data, in particular MPI measurement data, of a sample comprising magnetic particles within an examination volume (FOV) or providing virtual signal data that were obtained with an inverse transformation of a portion from an already previously established overall image data record;
reconstructing the MPI overall image data record from the MPI signal data and an appended system matrix, wherein a partial volume image data record is produced for each particle class.

The appended system matrix can be obtained by virtue of appending system matrices for different particle classes in one dimension, in particular in one spatial direction. According to the invention, ghost artifacts are identified by virtue of carrying out an inverse transform of a portion (selection region) of the reconstructed MPI overall image data record (selection region). The selection region denotes image data of an image region (region in real space) that is assigned to a certain region within the examination volume.

The selection region is set by virtue of certain image data of the reconstructed MPI overall image data record not being taken into account for the production of the virtual signal data. The inverse transformation of image data (real space) into (so-called virtual) signal data (frequency space) is therefore implemented by multiplying a portion of the MPI overall image data record selected according to the selection region by the appended system matrix or by multiplying the complete MPI overall image data record by a portion of the system matrix selected according to the selection region. The "virtual signal data" obtained by the inverse transformation are data in the frequency space that would be obtained with an MPI measurement if the image data of the selection region (including ghost artifacts) were to correspond to a sample to be imaged. Thus, the virtual signal data comprise signal data that would be obtained if the ghost artifacts contained in the selection region were not artifacts but, for example, really existing particle distributions.

Ghost artifacts are produced again by the following reconstruction of the virtual overall image data record, which is carried out in analogous fashion to the original reconstruction of the overall image data record, i.e., with the same appended system matrix. Since the virtual signal data are only related to the selection region, data should also only be reconstructed in the selection region in the case of an artifact-free reconstruction. The image region (region in real space) in which no image data should really be allowed to be reconstructed as no virtual signal data were produced therefor is referred to as artifact region.

Signals lying outside of the selection region in the virtual overall image data record, i.e., in the artifact region, can therefore be identified as artifact image data.

The selection region of the reconstructed MPI overall image data record comprises at least 1 voxel of the MPI overall image data record.

Preferably, the selection region comprises one partial volume or a plurality of partial volumes of the MPI overall image data record. Thus, the selection region is selected in such a way that, in step b), only image data from one partial volume or a plurality of partial volumes (but not all partial volumes) of the reconstructed MPI overall image data record are inverse transformed, for example by reducing the MPI overall image data record to a partial volume or a plurality of partial volumes, or by a corresponding reduction of the appended system matrix. This selection can be made without any a priori knowledge.

As an alternative thereto, provision can be made for the selection region only to comprise image regions of the reconstructed MPI overall image data record whose signal-to-noise ratio lies above a threshold. Thus, the selection region is then chosen in such a way that, in step b), only image regions of the reconstructed MPI overall image data record whose signal-to-noise ratio lies above a threshold are inverse transformed. With the correct choice of the SNR threshold, this can avoid a ghost artifact that causes another artifact (ghost-ghost artifact) in the artifact region during the reconstruction of the virtual MPI overall image data record being situated in the selection region.

In a particularly preferred variant of the method according to the invention, the selection region comprises the MPI overall image data record excluding a single partial volume. Thus, the selection region is then chosen in such a way that the MPI overall image data record excluding a single partial volume is inverse transformed. A single partial volume could be made artifact-free more quickly in this way since the ghost artifacts of all particle classes in the partial volume not contained in the selection region (artifact region) are produced in one step.

In an extreme case, the selection region can be chosen in such a way that all voxels of the overall image data record apart from a single voxel are inverse transformed.

In a specific variant, the selection region comprises only one or more image region(s) of the reconstructed MPI overall image data record in which a changed magnetic particle concentration is expected. Thus, the selection region is then chosen in such a way that only image regions in which a modified magnetic particle concentration is expected are inverse transformed. Here, this can be a region, for example, within which a catheter is moved.

In an alternative variant of the method, the selection region comprises an image region of the reconstructed MPI overall image data record, wherein this image region is established by virtue of a mapped overall image data record being reconstructed from signal data of a system matrix of a selected particle class and the appended system matrix and wherein only the part of the mapped overall image data record containing artifact concentrations above a threshold is set as an image region. Thus, the image region used as selection region is determined on the basis of the system matrix of a selected particle class or from the signal data (which were simulated or obtained from calibration measurement) which are contained in the system matrix, wherein all signal data (signal data recorded within the system matrix region, i.e., without background signal data) of a selected system matrix are summed in order to reconstruct a mapped overall image data record cmap(r) using the appended system matrix. As an alternative thereto, all signal data (signal data recorded within the system matrix region, i.e., without background signal data) of a selected system matrix can be reconstructed using the appended system matrix, wherein all reconstructed image data resulting therefrom are combined in a subsequent step to form a mapped overall image data record cmap(r) (e.g., via addition). This determination of the image region intended to serve as selection region can already be implemented before measuring the MPI signal data of the sample to be measured in actual fact. The concentration distribution of the selected particle class in a partial volume is reconstructed by reconstructing the mapped overall image data record. Moreover, ghost artifacts emerge in the other partial volumes. Ghost artifacts with an intensity above the threshold set the image region whose image coordinates should be used as selection region in the method according to the invention for establishing and/or reducing artifacts. A selection region (ghost region), in which an increased ghost artifact sensitivity is expected, is mapped herewith.

The invention also relates to a method for establishing a local concentration distribution of magnetic particles of different particle classes within an examination volume or a variable derived from this concentration distribution. According to the invention, artifact image data are established according to the above-described method. In a step f), a corrected overall image data record is established.

In a first variant of this method, steps a)-e) are repeated N−1 times (i.e., steps a)-e) are carried out N times), wherein the selection region is selected/set from the last-established corrected overall image data record in each repetition in step a). Here, the selection region is set in such a way that it is not equal to the selection region/selection regions set during the preceding iterations. An artifact data sum (e.g., sum of the artifact image data or sum of artifact signal data that were inverse transformed from these artifact image data) is established in step e) from the established artifact image data. The corrected overall image data record is established in step f) using the artifact data sum. In this case, the corrected overall image data record is a final corrected overall image data record since all ghost artifact corrections have already been taken into account. Preferably, steps a)-e) are repeated as often as necessary until artifact image data were established for the entire reconstructed MPI overall image data record.

In a second variant of the method according to the invention, steps a)-f) are repeated N−1 times, wherein the selection region in step a) is selected from the last established corrected overall image data record within the scope of each repetition. Here, the selection region is set in such a way that it is not equal to the selection region/selection regions set in preceding iterations. In this variant, a preliminary corrected overall image data record is produced in each iteration, said preliminary corrected overall image data record serving as a basis for the next iteration. Preferably, steps a)-f) are repeated as often as necessary until artifact image data were established for the entire reconstructed MPI overall image data record.

Preferably, N equals the number of system matrices comprised by the appended system matrix. Then, respectively one partial volume can be selected during each repetition.

Preferably, the artifact image data are subtracted from the image data of an overall image data record in step f) for the purposes of establishing the corrected overall image data record. In a variant 1, this subtraction is implemented once in the last iteration between the MPI overall image data record and the artifact data sum in the form of summed artifact image data (artifact image data sum). In variant 2, the subtraction is carried out in each iteration between the (MPI or preliminary) overall image data record used in the respective iteration and the artifact image data established in this iteration. In both cases, the correction of the overall image data record is carried out in real space.

As an alternative to correcting the overall image data record in real space, the correction can also be carried out in frequency space. Here, artifact signal data are subtracted from the signal data of an overall image data record. According to the invention, provision is made to this end for the following method steps to be carried out for the purposes of establishing the corrected overall image data record in step f):

inverse transforming the artifact image data into artifact signal data;
  establishing difference signal data by subtracting the artifact signal data from the signal data of an overall image data record;
  reconstructing the corrected overall image data record from the difference signal data and the appended system matrix.

Here, the inverse transformation of the artifact image data into the frequency space is implemented with the aid of the appended system matrix.

The correction in the frequency space can be carried out with both of the above-described variants 1 and 2. In variant 1, the artifact image data are either inverse transformed and summed or the sum of the artifact image data is inverse transformed. In both cases, an artifact signal data sum is formed. The difference signal data are established once in the last iteration by subtracting the artifact signal data sum from the MPI signal data in variant 1.

In variant 2, the artifact image data established in the respective iteration are inverse transformed and difference signal data are established in each iteration by subtracting the artifact signal data from the MPI signal data (in the first iteration) or by subtracting the artifact signal data from the difference signal data of the preceding iteration.

If use is made of the sum of all artifact image data, the method steps of inverse transforming the artifact image data, establishing difference signal data and reconstructing the corrected overall image data record thus only have to be carried out once.

Preferably, steps a)-f) are repeated as often as necessary until artifact image data were established for the entire reconstructed MPI overall image data record.

Preferably, the reconstruction/reconstructions is/are implemented in the sparse domain [Knopp].

The appended system matrix can be formed by appending projected system matrices, wherein the projected system matrices are produced by projecting system matrices along the same projection direction.

The appended system matrix can also be formed by appending a plurality of linked system matrices, wherein each of the linked system matrices is produced by an addition and/or a subtraction of system matrices.

The invention also relates to a system for visually representing a corrected overall image data record established according to an above-described method, said system comprising:
i) an MPI installation for detecting MPI signal data,
ii) an electronic storage medium containing a plurality of system matrices or a stored computer program configured to simulate system matrices of different particle classes,
iii) a stored computer program configured to carry out the above-described method, and
iv) an indicator apparatus (display), which presents the reconstructed MPI image data. Further advantages of the invention emerge from the description and the drawing. Likewise, according to the invention, the features specified above and the features yet to be explained below can find use, either respectively on their own or together in any combination. The shown and described embodiments should not be understood as a comprehensive list but instead have an exemplary character for illustrating the invention.

BRIEF DESCRIPTION OF THE DRAWINGS

FIG. 1 shows a schematic illustration of a system according to the invention.

FIG. 2 shows a flowchart of a method according to the prior art.

FIG. 3A shows a phantom MPI sample with different particle classes.

FIG. 3B schematically shows the overall image data record that should arise for the phantom MPI sample shown in FIG. 3A post reconstruction.

FIG. 3C schematically shows an overall image data record with partial volumes for each particle class of the phantom MPI sample shown in FIG. 3A, reconstructed with a method according to the prior art.

FIG. 4A, 4B show flowcharts of a first variant of the method according to the invention with corrections in real space.

FIG. 8 shows an alternative variant for determining a selection region with increased ghost artifact sensitivity according to a mapping method.

DETAILED DESCRIPTION

Figure 5A:
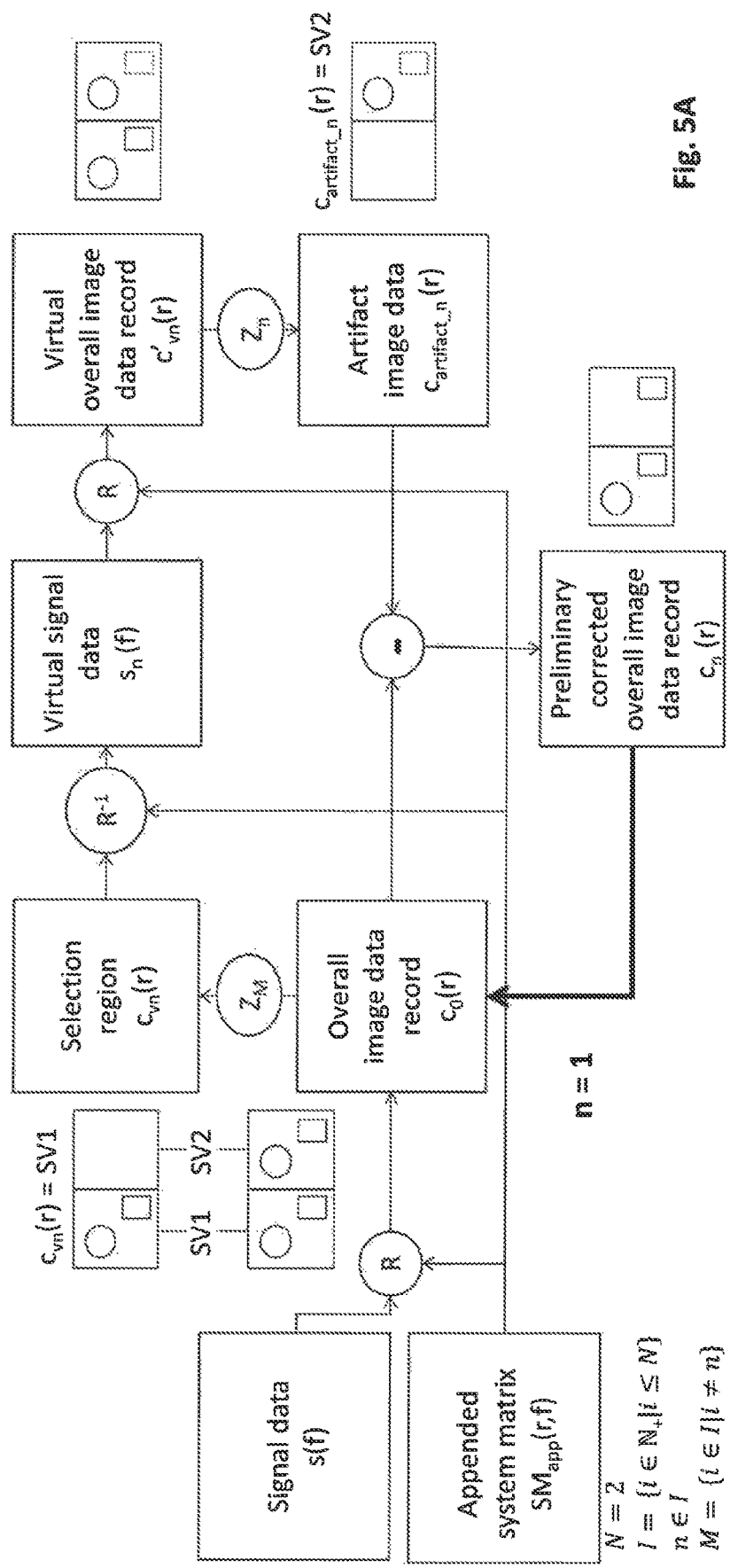
FIG. 5A, 5B show flowcharts of a second variant of the method according to the invention with corrections in real space.

The system according to the invention is shown in FIG. 1 and comprises an MPI installation 1 with coil arrangements 10, 11, 12 for producing a spatially dependent magnetic field and a magnetic drive field within an examination volume 13, as is known from U.S. Pat. No. 9,364,165 B2, for example. MPI signal data u(t) (signal data in the time domain) or s(f) (signal data in the frequency domain) are detected by the MPI installation 1. Moreover, the system according to the invention comprises a device 2 for generating an appended system matrix $SM_{app}$ from system matrices for different particle classes. The appended system matrix $SM_{app}$ and the MPI signal data u(t) or s(f) are supplied to a reconstruction device 3 (e.g., a linear solver) for the purposes of reconstructing an MPI overall image data record $c_{n-1}(r)$ (spatial domain) from the MPI signal data u(t) and s(f) and the appended system matrix $SM_{app}$. Ghost artifacts G1, G2 are eliminated or at least reduced from the MPI overall image data record $c_{n-1}(r)$ in a correction device 5 (for example, a stored computer program) such that a corrected MPI overall image data record is produced, it being possible to present the latter on an indicator apparatus 4 of the system according to the invention.

FIG. 2 shows the procedure of a method for visually presenting an overall image data record according to the prior art on the basis of an example of two system matrices $SM_1(r,f)$, $SM_2(r,f)$ for two different particle classes. The system matrices $SM_1(r,f)$, $SM_1(r,f)$ of the different particle classes are juxtaposed to form an appended system matrix $SM_{app}(r,f)$. Thus, a matrix with twice the size of the system matrices $SM_1(r,f)$, $SM_1(r,f)$ is formed. This appended system matrix $SM_{app}(r,f)$ is now used to reconstruct an MPI overall image data record c(r) from the measurement data s(f).

In an exemplary fashion, FIGS. 3A, 3B, 3C show a (phantom) MPI sample S which comprises different (in this case: two) particle classes P1, P2. Using the method according to the prior art shown in FIG. 2, the two particle classes P1, P2 can be visualized in different partial volumes SV1, SV2 of the MPI overall image data record c(r) (number of partial volumes=number of system matrices that were appended to create the appended system matrix; in this case: 2). If all system matrices have the same dimensions, the MPI overall image data record comprises N·x·y·z voxels (with x, y, z=number of voxels of the examination volume in the various spatial directions; N=number of system matrices that were appended to create the appended system matrix). In the case of a correct reconstruction, the particle distribution of respectively one particle class P1, P2 should be presented in each partial volume SV1, SV2. Thus, an artifact-free reconstruction should yield the image shown in FIG. 3B. However, if the two particle classes P1, P2 do not differ sufficiently from one another, part of the signal of particle class P1 is reconstructed as ghost artifact G1 in the partial volume SV2 of particle class P2 and part of the signal of particle class P2 is reconstructed as ghost artifact G2 in the partial volume SV1 of particle class P1, as illustrated in FIG. 3C. Using the method according to the invention presented below, such ghost artifacts G1, G2 can be eliminated or at least be reduced.

FIGS. 4A, 4B show flowcharts of iterations of a first variant of the method according to the invention with two iterations Like in the method known from the prior art, an overall image data record $c_0(r)$ is reconstructed with MPI signal data s(f) and an appended system matrix $SM_{app}$ in a reconstruction operation R in the first iteration shown in FIG. 4A. A corresponding overall image data record $c_0(r)$ with partial volumes SV1, SV2 is illustrated in exemplary fashion for the sample S shown in FIG. 3A. An overall image data record analogous to FIG. 3C emerges after the reconstruction R. According to the invention, a selection region $c_{vn}(r)$ is now selected from this overall image data record $c_0(r)$ within the scope of a selection operation $Z_M$, the partial volume SV1 in the present example. This selection region SV1 is now subjected to an inverse transformation $R^{-1}$ with the aid of the appended system matrix $SM_{app}$, as a result of which virtual signal data $s_n(f)$ are produced. A virtual overall image data record $c'_{vn}(r)$ is produced by a subsequent reconstruction operation R, which again is implemented with the aid of the appended system matrix $SM_{app}$. In addition to the image data of the selection region SV1 (particle distribution of particle class P1, ghost artifact G2), ghost artifact G1 (artifact of the particle distribution of particle class P1 reconstructed in partial volume SV1 of the overall image data record $c_0(r)$) and ghost-ghost artifact G2' (ghost artifact of the ghost artifact G2 reconstructed in the partial volume SV1 of the overall image data record $c_0(r)$) are generated during the reconstruction R in the partial volume SV2 (i.e., outside of the selection region $c_{vn}(r)$). Since it is known on account of the previously set selection region (partial volume SV1) that no image data should have actually been reconstructed in partial volume SV2, the image data G1, G2' of the virtual overall image data record $c'_{vn}(r)$ reconstructed in partial volume SV2 can be identified as artifact image data $c_{artifact\_n}(r)$. This is implemented within the scope of an identification operation $Z_n$.

Subsequently, a (preliminary) artifact image data sum $c_{artifact}(r)$ is formed. Since FIG. 4A is the first iteration, the identified artifact image data $c_{artifact\_n}(r)$ form the artifact image data sum $c_{artifact}(r)$. After establishing the artifact image data sum $c_{artifact}(r)$ for the first iteration, a second selection region (in this case second partial volume SV2) that differs from the first selection region SV1 is set, as shown in FIG. 4B. The same method steps (inverse transforming virtual signal data $s_n(f)$, reconstructing a virtual overall image data record $c'_{vn}(r)$, identifying artifact image data $c_{artifact\_n}(r)$, establishing the artifact image data sum $c_{artifact}(r)$) as described above are carried out for the second selection region SV2. The method is continued until all selection regions $c_{vn}(r)$ of interest were processed accordingly. The artifact image data sum $c_{artifact}(r)$ then comprises the artifact image data (G1, G2, G1', G2') from all selection regions $c_{vn}(r)$. In the last iteration of the method according to the invention, the last-established artifact image data sum $c_{artifact}(r)$ is subtracted from the overall image data record $c_0(r)$, as shown in FIG. 4B. A corrected overall image data record $c_N(r)$ emerges, which ideally only still represents the particle concentrations of the particle classes P1, P2. Thus, the ghost artifacts G1, G2 are removed from the originally established overall image data record $c_0(r)$ by the final subtraction operation.

Figure 5B:
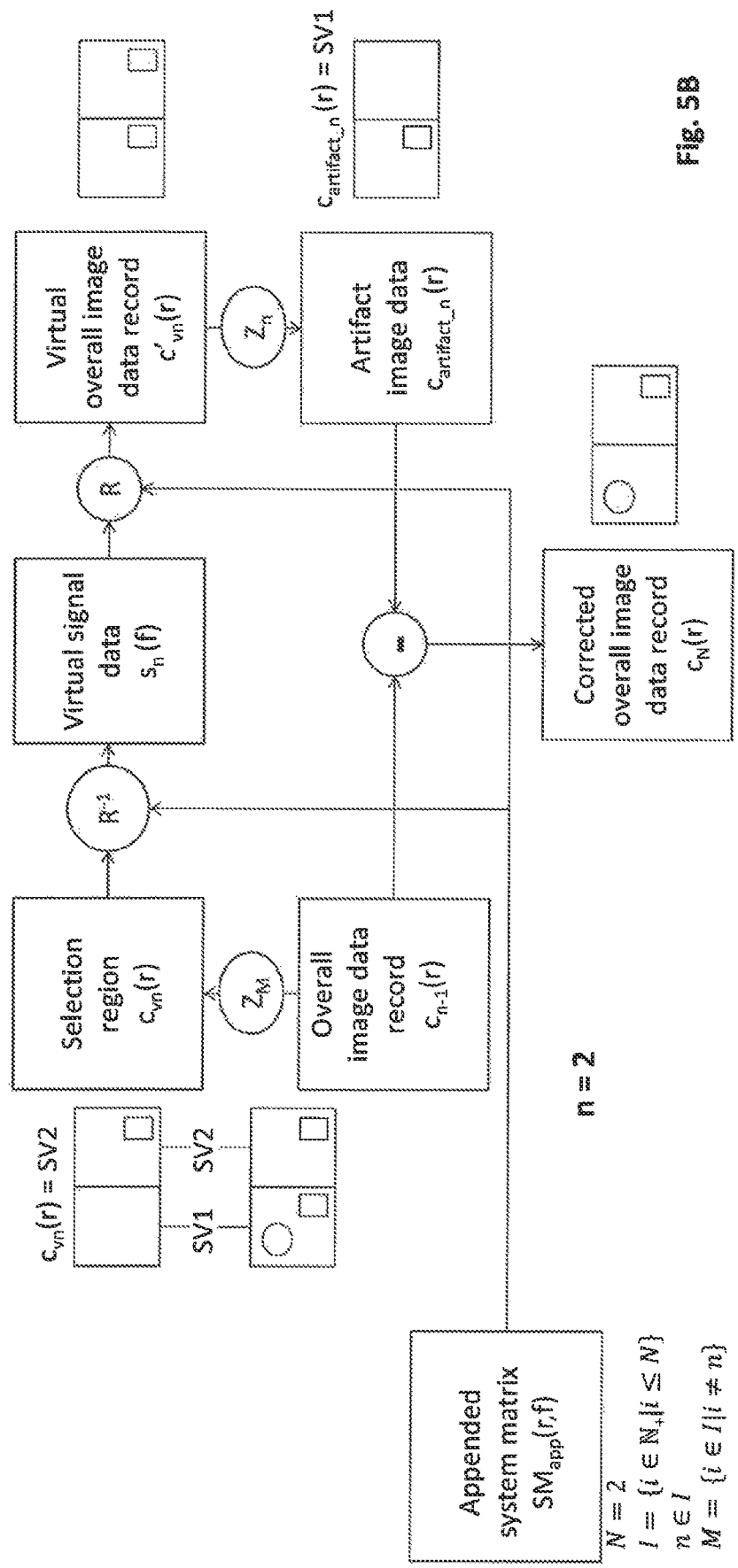

FIGS. 5A, 5B show a second variant of the method according to the invention (also in exemplary fashion with two iterations in this case), in which, in each iteration, the artifact image data $c_{artifact\_n}(r)$ identified in this iteration are subtracted from the overall image data record $c_{n-1}(r)$ used in this iteration (from $c_0(r)$ in the first iteration). In this way, a preliminary corrected overall image data record $c_n(r)$ is produced in each iteration. The preliminary corrected overall image data record of the first iteration is used as overall image data record of the second iteration (FIG. 5B), from which the second selection region (in this case: partial volume SV2) is selected. Consequently, the corrected overall image data record $c_N(r)$ is produced in the last iteration (the second iteration in this case; FIG. 5B). The preliminary corrected overall image data record $c_{n-1}(r)$ serving in FIG. 5B as a basis for setting the selection region has fewer ghost artifacts than the overall image data record $c_0(r)$ originally used in the first iteration since ghost artifact G1 was removed by correction in the first iteration.

Thus, artifacts which, during the reconstruction R of each particle class P1, P2, are produced in the part of the reconstructed region not comprising the selection region are determined individually and subtracted from the overall image data record of the preceding iteration in the second method variant. In this way, the ghost artifacts of the various particle classes can be corrected successively.

Figure 6A:
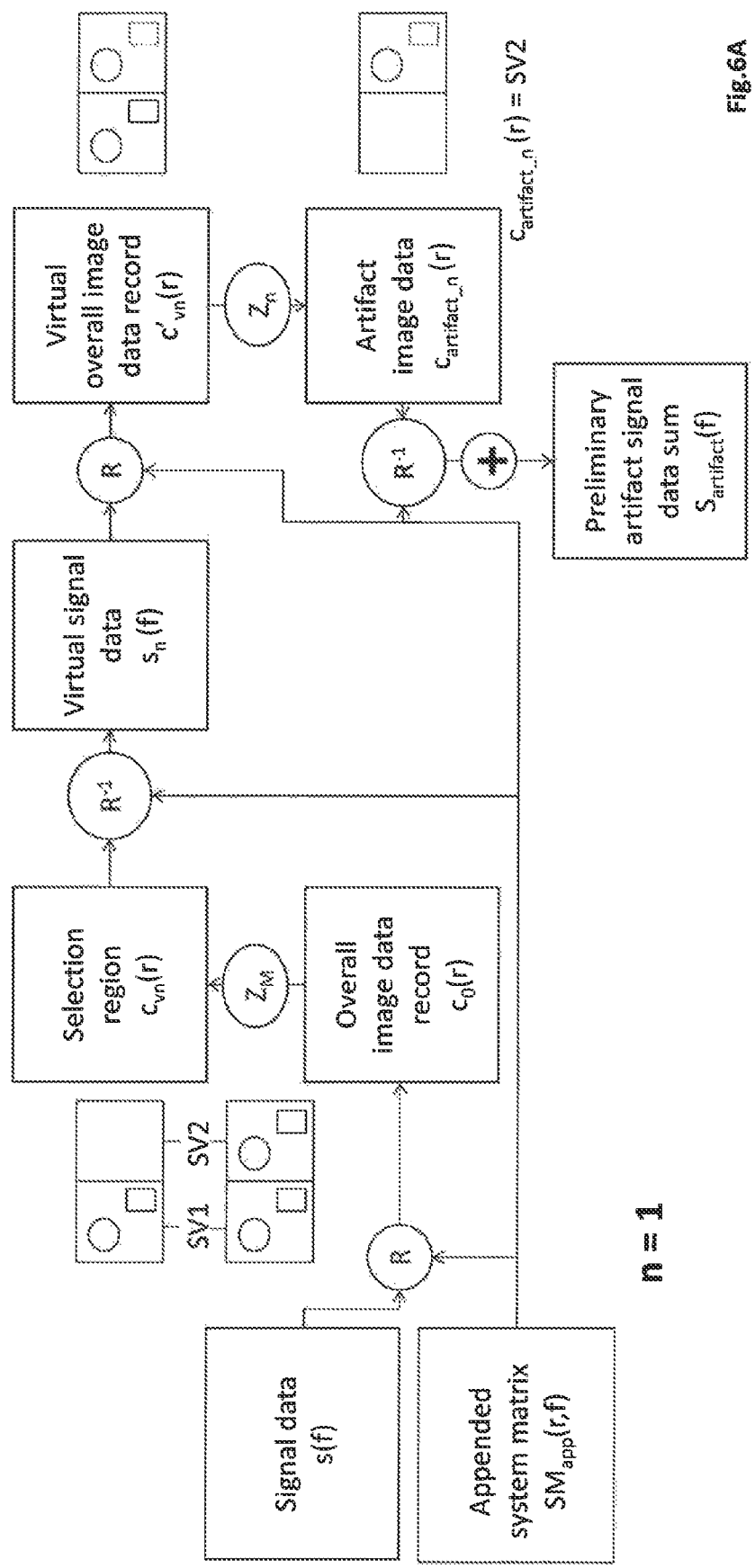
FIG. 6A, 6B show flowcharts of a first variant of the method according to the invention with corrections in frequency space.
Figure 6B:
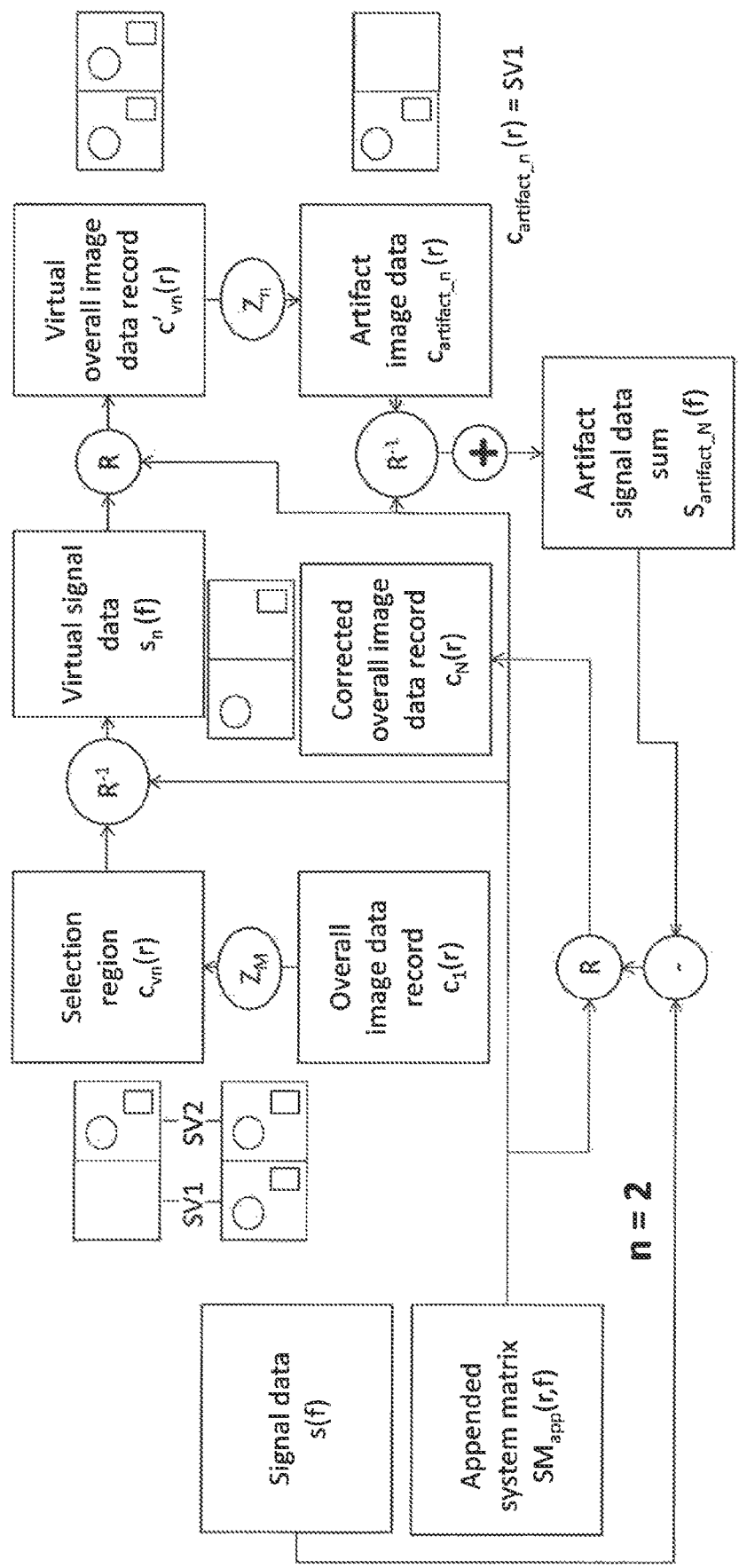

FIGS. 6A, 6B show a modification of the first method variant, in which the correction is carried out in frequency space rather than real space. To this end, the artifact image data $c_{artifact\_n}(r)$ are transformed into frequency space as artifact signal data in each iteration with an inverse transformation operation $R^{-1}$. These artifact signal data are then summed to form a preliminary artifact signal data sum $S_{artifact}(f)$. In the last iteration (FIG. 6B), the artifact signal data sum $S_{artifact}(f)$ established in this iteration is subtracted from the original signal data s(f). Then, the corrected overall image data record $c_N(r)$ is produced by a reconstruction operation R.

Figure 7A:
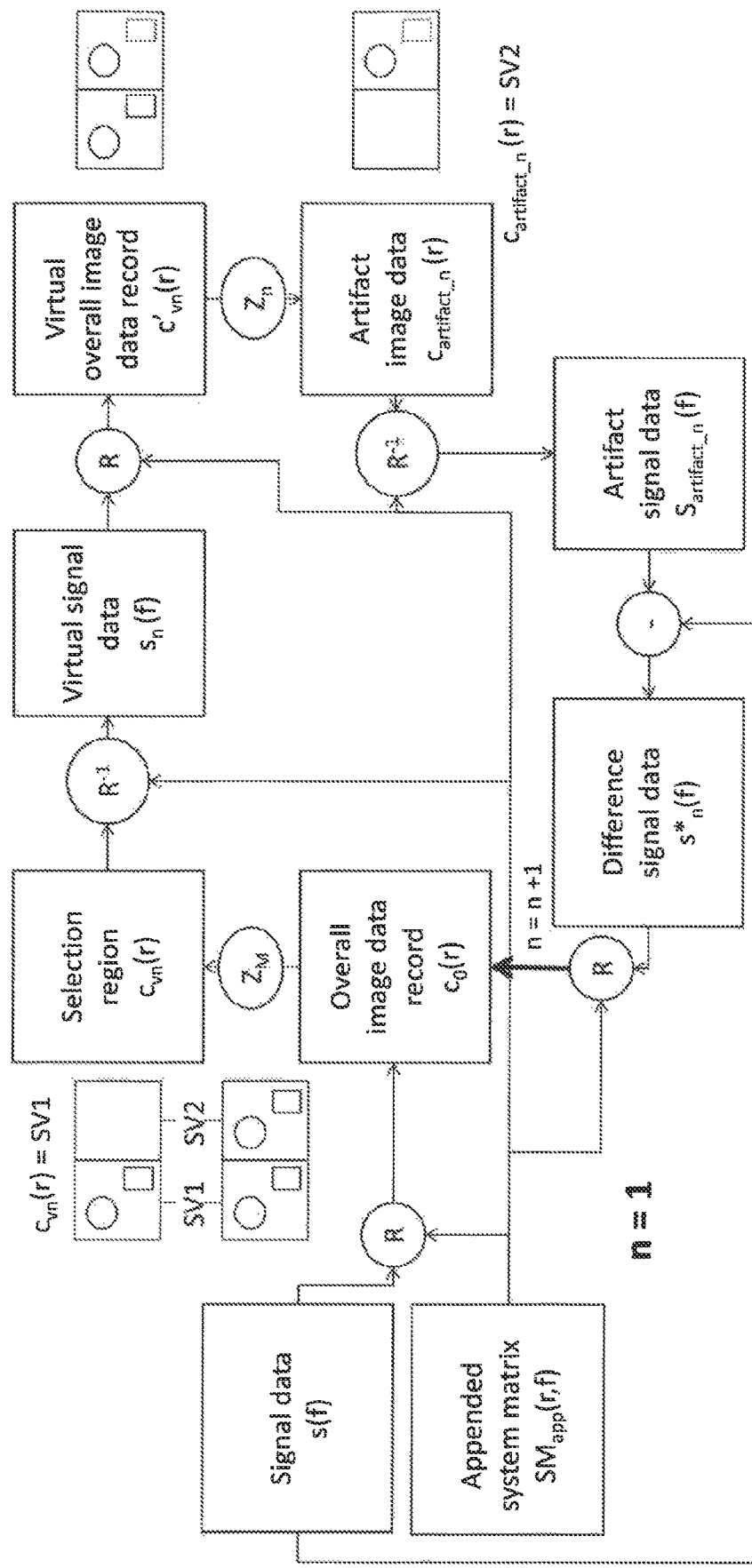
FIG. 7A, 7B show flowcharts of a second variant of the method according to the invention with corrections in frequency space.
Figure 7B:
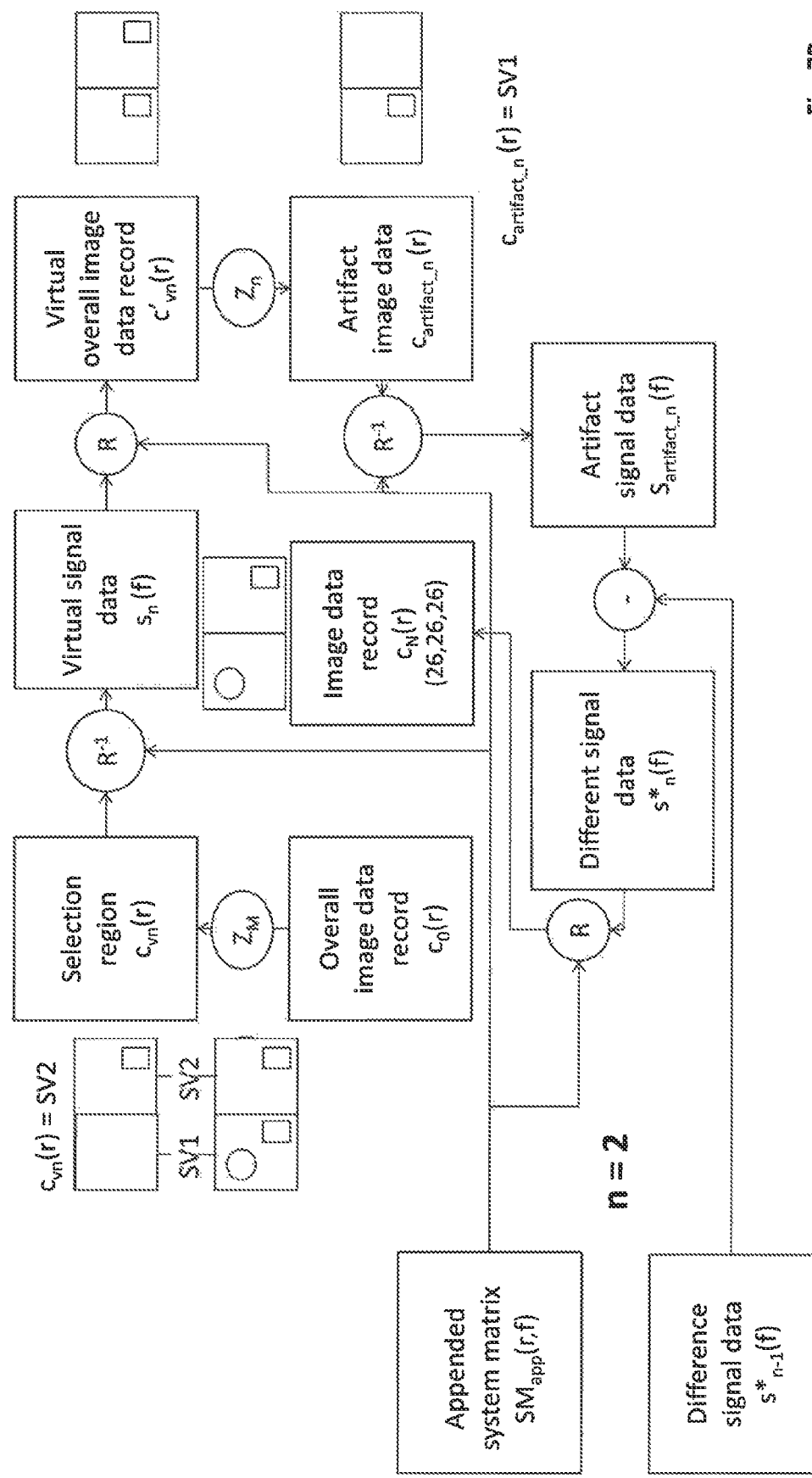

The second method variant can also be modified in similar fashion, as shown in FIG. 7A and FIG. 7B. Here, too, the artifact image data $c_{artifact\_n}(r)$ established in the respective iteration are inverse transformed into frequency space by an inverse transformation operation $R^{-1}$, and so artifact signal data $S_{artifact\_n}(f)$ are generated. In contrast to the variant shown in FIG. 6A, FIG. 6B, the artifact signal data are not, however, summed here; instead, in each iteration, the artifact signal data $S_{artifact\_n}(f)$ established in this iteration are subtracted from the signal data (in FIG. 7A: s(f); in further iterations: $s^*_n(f)$) from which the overall image data record (FIG. 7A: $c_0(r)$; in general: $c_{n-1}(r)$) used in this iteration was established. In this way, difference signal data $s^*_n(f)$ are produced in each iteration. A preliminary corrected overall image data record ($c_{n-1}(r)$ in FIG. 7B) is produced from these difference signal data $s^*_n(f)$ using a reconstruction operation R, said preliminary corrected overall image data record then forming the basis for setting the selection region in the next iteration. The image data record reconstructed from the difference signal data in the last iteration (FIG. 7B) forms the corrected overall image data record $c_N(r)$.

FIG. 8 shows the method for determining the selection region ($c_{vn}(r)$) according to the mapping method. To this end, a reconstruction is initially carried out with signal data of a system matrix ($SM_n(r,f)$) of a selected particle class and with the appended system matrix ($SM_{app}(r,f)$). By way of example, if the point sample that was used to create the system matrix ($SM_n(r,f)$) contains signal components that fit to the individual appended system matrices, concentrations are reconstructed in the respective partial volumes (two partial volumes (SV1 and SV2) in the example of FIG. 8). The mapped overall image data record ($C_{map}(r)$) that arose hereby can thus be subdivided into partial volumes that correspond to the number of appended individual matrices in the appended system matrix ($SM_{app}(r,f)$).

Two partial volumes (SV1 and SV2) are illustrated in exemplary fashion in FIG. 8, wherein the left-hand partial volume (SV1) images a concentration distribution corresponding to the system matrix ($SM_n(r,f)$) as the latter was created for calibration purposes, for example with the aid of a point sample over the system matrix range. The right-hand partial volume (SV2), by contrast, only shows the artifact region, wherein the artifact concentration may be distributed unevenly over the right-hand partial volume (SV2). Therefore, for the purposes of establishing a reconstructed image region with an increased ghost artifact sensitivity (SV2') in the partial volume (SV2) of the mapped overall image data record ($C_{map}(r)$), a threshold is used, said threshold defining the regions in which the artifact concentration is too high. In this way, the image region (SV2') in which an increased ghost artifact sensitivity is expected is defined. This image region or the coordinates of this image region can serve as selection region in the previously shown variants of the method according to the invention.

Figure 9:
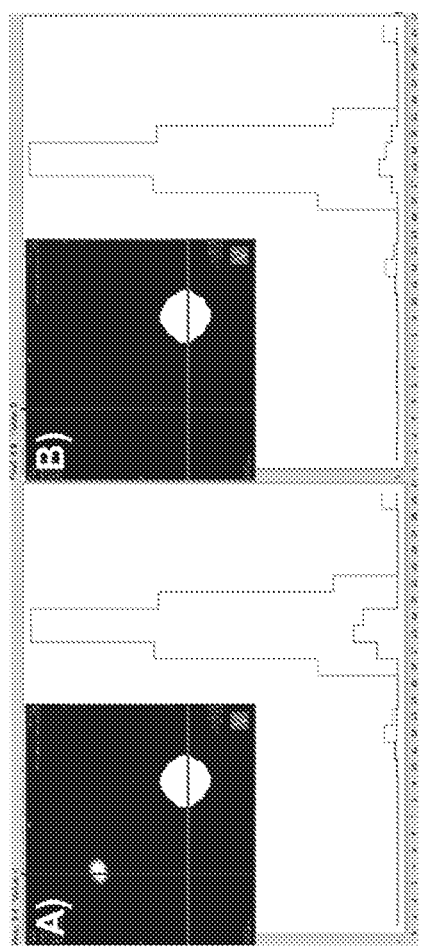
FIG. 9 shows a reconstructed image data record and sectional profiles of an image data record reconstructed by a standard multi-parameter reconstruction method and of an image data record corrected and reconstructed by the method according to the invention.

FIG. 9 shows, in region A, an experimentally obtained image of a layer of an image volume, wherein the image data were reconstructed using a conventional reconstruction method. In addition to the elevated signal at the actual particle position (bottom right), it is possible to identify a ghost artifact (top left). FIG. 9 shows, in region B), the same layer of the image volume, wherein the data were subjected to a correction with the method according to the invention. It is possible to identify that the intensity of the ghost artifact is greatly reduced by the application of the method according to the invention. The sectional profiles through the particle position and the ghost artifact are likewise illustrated in FIG. 9, regions A) and B).

All method variants are based on an iterative method, wherein, in each case, a selection region is set from the overall image data record and inverse transformed, wherein the effects of a subsequent reconstruction on the non-selected region can be identified in the form of ghost artifacts. In this way, all ghost artifacts produced by the reconstruction of the various selection regions can be identified step-by-step and the overall image data record can be corrected accordingly.

LIST OF REFERENCE SIGNS

1 MPI installation
2 Device for generating an appended system matrix
3 Reconstruction device (linear solver)
4 Indicator apparatus
5 Correction device
10, 11, 12 Coil arrangements
13 Examination volume
$c_n(r)$ MPI overall image data record
c(r) MPI overall image data record according to the prior art
P Projection operation
R Reconstruction operation
u(t) MPI signal data (time domain)
s(f) MPI signal data (frequency domain)
$c_n(r)$ MPI overall image data record
$c_N(r)$ Corrected MPI overall image data record
$C_{map}(r)$ Mapped MPI overall image data record
$SM_{app}(r,f)$ Appended system matrix
$SM_a(r,f)$ System matrix for particle class P1
$SM_b(r,f)$ System matrix for particle class P2
SV1 Partial volume of particle class 1
SV2 Partial volume of particle class 2
SV2' Reconstructed image region with increased ghost artifact sensitivity in the partial volume of particle class 2
P1 Particle class 1
P2 Particle class 2
G1 Ghost artifact of particle class 1 in partial volume 2
G1' Ghost-ghost artifact of virtual signal data of partial volume 2 in partial volume 1
G2 Ghost artifact of particle class 2 in partial volume 1
G2' Ghost-ghost artifact of virtual signal data of partial volume 1 in partial volume 2
$C_{artifact\_n}$ Artifact image data of an iteration
$C_{artifact}$ Artifact image data sum
$Z_M$ Selection operation
$Z_n$ Identification operation

CITATIONS

[Rahmer] Rahmer et al., First experimental evidence of the feasibility of multi-color magnetic particle imaging"; Phys. Med. Biol. 60 (2015) 1775-1791 DOI: 1031088/0031-9155/60/5/1775

[Stehning] Stehning et al. "Simultaneous Magnetic Particle Imaging (MPI) and Temperature Mapping Using Multi-Color MPI." International Journal on Magnetic Particle Imaging 2, no. 2 (2016). https://journal.iwmpi.org/index.php/iwmpi/article/view/34; FIG. 6

[Grüttner] Grüttner et al. "On the formulation of the image reconstruction problem in magnetic particle imaging"; Biomedical Engineering/Biomedizinische Technik; Volume 58, Issue 6 (December 2013); DOI: https://doi.org/10.1515/bmt-2012-0063)

[Knopp] Knopp et al. "Sparse Reconstruction of the Magnetic Particle Imaging System Matrix" EEE Transactions on Medical Imaging; Volume: 32 Issue: 8; DOI: 10.1109/TMI.2013.2258029

U.S. Pat. No. 9,364,165 B2

US 2012/0197115 A1

What is claimed is:

1. A method for establishing and/or reducing artifacts that arise when reconstructing a magnetic particle imaging (MPI) overall image data record ($c_0(r)$) from MPI signal data and an appended system matrix ($SM_{app}(r,f)$), wherein the appended system matrix comprises system matrices ($SM_1(r,f)$, $SM_2(r,f)$) of different particle classes (P1, P2), wherein the method comprises:
   a) setting a selection region ($c_{vn}(r)$) of a reconstructed MPI overall image data record ($c_{n-1}(r)$; ($c_0(r)$);
   b) producing virtual signal data ($s_n(f)$) by inverse transformation of the selection region ($c_{vn}(r)$);
   c) reconstructing a virtual overall image data record ($c'_{vn}(r)$) from the virtual signal data ($s_n(f)$) and the appended system matrix ($SM_{app}(r,f)$);
   d) setting an artifact region within the reconstructed virtual overall image data record ($c'_{vn}(r)$) such that the artifact region comprises only voxels lying outside of the selection region ($c_{vn}(r)$); and
   e) assigning the image data present in the artifact region as artifact image data ($c_{artifact\_n}(r)$).

2. The method as claimed in claim 1, wherein the selection region ($c_{vn}(r)$) comprises one partial volume (SV1, SV2) or a plurality of partial volumes (SV1, SV2) of the MPI overall image data record ($c_{n-1}(r)$; ($c_0(r)$).

3. The method as claimed in claim 1, wherein the selection region ($c_{vn}(r)$) comprises only image regions of the reconstructed MPI overall image data record ($c_{n-1}(r)$; ($c_0(r)$) whose signal-to-noise ratio lies above a threshold.

4. The method as claimed in claim 1, wherein the selection region ($c_{vn}(r)$) comprises the MPI overall image data record ($c_{n-1}(r)$; ($c_0(r)$) excluding a single one of the partial volumes (SV1, SV2).

5. The method as claimed in claim 1, wherein the selection region ($c_{vn}(r)$) comprises an image region of the reconstructed MPI overall image data record ($c_{n-1}(r)$; ($c_0(r)$) containing an expected change in magnetic particle concentration.

6. The method as claimed in claim 1, wherein the selection region ($c_{vn}(r)$) comprises an image region of the reconstructed MPI overall image data record ($c_{n-1}(r)$; ($c_0(r)$), wherein the image region is established by reconstructing a mapped overall image data record from a signal data of a system matrix of a selected particle class and the appended system matrix ($SM_{app}(r,f)$), and wherein only a part (SV2') of the mapped overall image data record containing artifact concentrations above a threshold is set as the image region.

7. A method for establishing a local concentration distribution of magnetic particles of different particle classes (P1, P2) within an examination volume or a variable derived from this concentration distribution, comprising:
   establishing the artifact image data ($c_{artifact\_n}(r)$) as claimed in claim 1, and
   f) establishing a corrected overall image data record ($c_n(r)$).

8. The method as claimed in claim 7, further comprising:
   repeating the steps a)-e) N−1 times, wherein a selection region that is not equal to the previously set selection region is set when repeating step a),
   wherein an artifact data sum ($c_{artifact}(r)$; $s_{artifact}(f)$) is established in step e) from the established artifact image data ($c_{artifact\_n}(r)$), and
   wherein the corrected overall image data record ($c_N(r)$) is established in step f) with the artifact data sum ($c_{artifact}(r)$; $s_{artifact}(f)$).

9. The method as claimed in claim 7, further comprising:
   repeating the steps a)-f) N−1 times, wherein the selection region ($c_{vn}(r)$) in step a) is selected from a last established corrected overall image data record ($c_{n-1}(r)$) within the scope of each repetition, wherein the selection region is not equal to the previously set selection region/selection regions.

10. The method as claimed in claim 8, wherein N equals the number of system matrices comprised by the appended system matrix ($SM_{app}(r,f)$).

11. The method as claimed in claim 9, wherein N equals the number of system matrices comprised by the appended system matrix ($SM_{app}(r,f)$).

12. The method as claimed in claim 7, wherein the artifact image data ($c_{artifact\_n}(r)$) are respectively subtracted from the image data of the MPI overall image data record ($c_{n-1}(r)$; $c_0(r)$) in the step f) for establishing the corrected overall image data record ($c_n(r)$; $c_N(r)$).

13. The method as claimed in claim 12, further comprising, for establishing the corrected overall image data record ($c_n(r)$; $c_N(r)$) in the step f):
   inverse transforming the artifact image data ($c_{artifact\_n}(r)$) into artifact signal data;
   establishing difference signal data ($s^*_n(f)$) by subtracting the artifact signal data from the signal data ($s(f)$, $s^*_{n-1}(f)$) of an overall image data record ($c_0(r)$, $c_{n-1}(r)$);
   reconstructing the corrected overall image data record from the difference signal data ($s^*_n(f)$) and the appended system matrix ($SM_{app}(r,f)$).

14. The method as claimed in claim 1, wherein the reconstruction is implemented in a sparse domain.

15. The method as claimed in claim 1, wherein the appended system matrix ($SM_{app}(r,f)$) is formed by appending projected system matrices, wherein the projected system matrices are produced by projecting system matrices along same projection direction.

16. The method as claimed in claim 1, wherein the appended system matrix ($SM_{app}(r,f)$) is formed by appending a plurality of linked system matrices, wherein each of the linked system matrices is produced by an addition and/or a subtraction of system matrices.

17. A system for visually representing a corrected overall image data record, comprising:
   i) an MPI installation configured to detect MPI signal data ($s(f)$),
   ii) an electronic storage medium containing a plurality of system matrices or a stored computer program configured to simulate system matrices of different particle classes,
   iii) a stored computer program configured to perform the method as claimed in claim 7, and
   iv) an indicator apparatus configured to display the reconstructed MPI image data.

* * * * *